US007001593B2

(12) United States Patent
Narasimhan et al.

(10) Patent No.: US 7,001,593 B2
(45) Date of Patent: *Feb. 21, 2006

(54) METHOD AND COMPOSITIONS FOR BLEACHING HAIR

(75) Inventors: Saroja Narasimhan, Matawan, NJ (US); Teresita Vergara Imperial, Staten Island, NY (US); Louann Christine Vena, Scotch Plains, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 35 days.

This patent is subject to a terminal disclaimer.

(21) Appl. No.: 10/752,062

(22) Filed: Jan. 7, 2004

(65) Prior Publication Data

US 2004/0141931 A1    Jul. 22, 2004

Related U.S. Application Data

(63) Continuation of application No. 10/115,497, filed on Apr. 3, 2002, now Pat. No. 6,703,004.

(51) Int. Cl.
 *A61K 7/135* (2006.01)
(52) U.S. Cl. ...................... 424/62; 424/70.6
(58) Field of Classification Search ............... 424/70.6, 424/70.1
 See application file for complete search history.

(56) References Cited

U.S. PATENT DOCUMENTS

| | | | |
|---|---|---|---|
| 5,575,989 A | 11/1996 | Caskey | 424/62 |
| 5,674,476 A | 10/1997 | Clausen | 424/62 |
| 5,888,484 A | 3/1999 | Schmitt | 424/62 |
| 5,891,423 A | 4/1999 | Weeks | 424/62 |
| 5,989,530 A | 11/1999 | Lorenz | 424/62 |
| 6,238,653 B1 * | 5/2001 | Narasimhan et al. | 424/62 |
| 6,315,989 B1 | 11/2001 | Narasimhan | 424/62 |
| 6,613,311 B1 * | 9/2003 | Imperial | 424/62 |
| 6,703,004 B1 * | 3/2004 | Narasimhan et al. | 424/62 |

OTHER PUBLICATIONS

Robbins, Clarence R., *Chemical and Physical Behavior of Human Hair*, Chapter 4, pp. 67-69, Dec. 2001.
Mohile, R.B., *Hair Care: Benefit of Coconut Oil Relavance to Hair Damage*, Part III; Journal of Cosmetic Science, vol. 50, Nov./Dec. 1999.
Vaughan, C.D., *Using Solubility Parameters in Cosmetics Formulation*, Jounal of Society of Cosmetics Chemists, vol. 36, pp. 319-333, Sep./Oct. 1985.
Vaughan, C.D. *Solubility Effects in Product, Package, Penetration, and Preservation*, Cosmetics and Toiletries, vol. 133, pp. 47-69, Oct. 1988.
Grulke, Eric A., Solubility Parameter Values, vol. VII, pp. 519-557, Jan. 1, 2000.
Feria, The New Language of Color, package copy and ingredient labeling, Jan. 1, 2000.
Garnier Nutrisse Lightening Kit, package copy and ingredient labeling, Jan. 1, 2000.
Clairol Herbal Essences, Bleach Blonding, package copy and ingredient labeling, Jan. 1, 2000.
Clairol XtremeFX, Industrial Bonde, package copy and ingredient labeling, Jan. 1, 2000.
Feria 200, The New Language of Color, package copy and ingredient labeling, Jan. 1, 2000.
Clairol Maxi Blonde, package copy and ingredient labeling, Jan. 1, 2000.
Frost and Glow, Dramatic All Over Bleach Blonding Kit, package copy and ingredient labeling, May 15, 2001.

* cited by examiner

*Primary Examiner*—Jyothsna Venkat
(74) *Attorney, Agent, or Firm*—Julie Blackburn

(57) ABSTRACT

An emulsion hair bleach composition prepared by combining an aqueous oxidizing agent composition, a persulfate composition, and, optionally, a bleach oil composition, in amounts sufficient to provide a mixture containing an active oxygen concentration of about 3 to 5% by weight of the total mixture, a total alkalinity concentration of about 0.7–1.2 meq/gm., and 0.5–20% by weight of the total mixture of an oil having a solubility parameter of 5–12 $(cal/cm^3)^{1/2}$; an emulsion hair bleach composition capable of lightening hair in 10 to 30 minutes, and a kit for use in bleaching hair.

30 Claims, No Drawings

METHOD AND COMPOSITIONS FOR BLEACHING HAIR

This is a continuation of application(s) Ser. No. 10/115,497, filed Apr. 3, 2002 now U.S. Pat. No. 6,703,004.

TECHNICAL FIELD

The invention is in the field of methods and compositions for bleaching hair.

BACKGROUND OF THE INVENTION

Women have been bleaching their hair for thousands of years. Some of the primitive concoctions used to bleach hair in early Rome, prior to the beginning of the Christian era, included native minerals such as alum, soda, and wood ash combined with wine dregs or water. Such preparations were often left on the hair for several days, and lightened very dark hair to a desirable reddish gold in color. A number of books published during the Renaissance also disclose various formulas for bleaching hair. Typically these compositions were based upon ingredients such as alum, borax, or soda, in combination with plant extracts. It has also been reported that Venetian women obtained their blond hair by sponging it with a solution of soda (or rock alum, black sulfur, and honey) through the hair, spread it over the broad brim of a crownless hat, and let it dry in the sunlight [Cosmetics: Science and Technology, Second Edition, Volume 2, 1972]. This treatment persisted for hundreds of years thereafter, until the fashions changed.

Modern hair bleaches are much milder and non-toxic when compared to their historical counterparts. The key ingredient is a mild oxidizing agent, which is most often hydrogen peroxide. Hydrogen peroxide exerts both a chemical and physical effect on the hair. It is capable of penetrating the hair cuticle and oxidizing the melanin (which provides color) so that the hair becomes noticeably lighter. If treated for a long enough period of time, hair can be colored to very light blonde or white, although it has been said that hair bleached with hydrogen peroxide only may tend to exhibit a yellowish tinge.

Currently, hair bleaches are most commonly found in the two component kit form. One component comprises an aqueous based hydrogen peroxide containing solution or emulsion. The second component comprises a powdered bleach composition that contains persulfate salts which act as accelerators of the bleaching process when the two components are combined. The hydrogen peroxide and persulfates are very reactive when combined and form nascent oxygen in addition to hydrogen and sodium sulfide. The nascent oxygen greatly facilitates oxidizing and bleaching of melanin from the hair. Typical bleaches generally have a pH of 9 to 11 and are applied to hair for 30 to 60 minutes to achieve the desired results.

While modern bleaches are significantly improved when compared to their pre-historic counterparts, there are still many need gaps in the standard bleaching process. One chronic consumer complaint is that the bleaching process takes too long. The 30 to 60 minutes required is simply too inconvenient for modern time-pressed consumers. In addition, the high pH and oxidizing agents may cause damage to those who have overly sensitive hair, particularly with repeat procedures. Accordingly, the gold standard for hair bleach is to provide bleach compositions that work in as short a time period as possible without damaging the hair, and at the same time achieving optimal lightening of hair.

It has been discovered that if the bleach composition applied to the hair has certain specific properties, the amount of time required to bleach the hair can be significantly reduced and the resulting composition is much "kinder" to the hair, even providing a conditioning effect.

Three parameters have been defined as contributing to a shorted time period to achieve hair bleaching. The first parameter is the active oxygen concentration in the bleach composition. As previously noted, it is nascent, or active, oxygen that causes bleaching of the melanin in the hair fiber. If the bleach composition does not contain an adequate level of active oxygen, the bleach will not adequately lighten hair. The second parameter is total alkalinity concentration. It has been found that the proper concentration of alkaline ingredients promotes opening of the hair cuticle and facilitates penetration of active oxygen into the hair fiber. Compositions that do not exhibit sufficient alkalinity are not as effective in lightening hair because the hair cuticle is not as penetrable. However, the amount of total alkalinity cannot be too high otherwise the composition can potentially cause irritation to skin and scalp. The third parameter that has an impact on optimal bleaching of the hair is the presence of a hydrophobic oil in the bleach composition. It has been discovered that the hydrophobic oil promotes more effective penetration of the active components into the hair shaft. Without being bound by this explanation, it is believed that the hydrophilic, water soluble bleach active ingredients are preferentially absorbed into the hair shaft because of their insolubility and incompatibility with the hydrophobic oil which "pushes" the water soluble ingredients away and into the hair shaft. The hydrophobic oil then deposits on the hair fibers and exerts a conditioning effect.

It is an object of the invention to provide a bleach composition that bleaches the hair in a reduced amount of time, prepared by combining an aqueous oxidizing agent composition, a persulfate composition, and optionally, an oil composition.

It is a further object of the invention to provide a bleach composition that contains a hydrophobic oil in an amount sufficient to cause preferential penetration of active ingredients into the hair shaft.

It is a further object of the invention to provide a bleach composition that also conditions the hair.

SUMMARY OF THE INVENTION

The invention is directed to an emulsion hair bleach composition prepared by combining (i) an aqueous oxidizing agent composition, (ii) a persulfate composition, and, optionally, (iii) a bleach oil composition, in amounts sufficient to provide a mixture containing:

(a) an active oxygen concentration of about 3 to 5% by weight of the total mixture, (b) a total alkalinity concentration of about 0.7–1.2 meq/gm., and (c) 0.5–20% by weight of the total mixture of an oil having a solubility parameter of 5–12 $(cal/cm^3)^{1/2}$.

The invention is also directed to an emulsion hair bleach composition prepared by combining (i) an aqueous oxidizing agent composition, (ii) a persulfate composition, and (iii) a bleach oil composition containing at least one hydrophobic oil having a Hildebrand solubility parameter ranging from about 5 to 12; in amounts sufficient to provide a mixture capable of lightening the hair in ten to thirty minutes.

The invention is also directed to a kit for use in bleaching hair comprising three separate components, wherein the first component is an aqueous oxidizing agent composition, the second component is a persulfate composition, and the third composition is a bleach oil composition containing at least one hydrophobic oil having a Hildebrand solubility parameter ranging from about 5 to 12; wherein when said three components are mixed they provide a composition that is operable to lighten hair in ten to thirty minutes.

DETAILED DESCRIPTION

I. The Mixture

The hair bleach composition of the invention is prepared by combining an aqueous oxidizing agent composition, a persulfate composition, and, optionally, a bleach oil composition, mixing well, and applying to the hair. The phrase "total mixture" when referred to "by weight of the total mixture" means the mixture obtained by combining the aqueous oxidizing agent composition, the persulfate composition, and, optionally, the bleach oil composition.

A. Active Oxygen

The mixture comprises an active oxygen concentration of about 3 to 5%, preferably about 3.2 to 4.8%, preferably about 3.5 to 4.5% by weight of the total mixture. The active oxygen present in the mixture is derived from ingredients that, when reacted, are capable of generating active, or nascent oxygen. Such ingredients include the following:

(1) Ingredients Contributing to Active Oxygen Concentration (i). Peroxide Oxidizing Agents Various peroxide oxidizing agents include hydrogen peroxide, urea peroxide, and the like.

(ii) Persulfates

Various alkaline earth metal, alkali metal, or ammonium persulfate such as sodium, potassium, ammonium persulfates are suitable. Preferably the persulfate comprises one or more of an alkali metal, alkaline earth metal, or ammonium persulfate. Examples of alkali metal persulfates include lithium, sodium, potassium, cesium, and the like. Examples of suitable alkaline earth metals include magnesium, calcium, and the like. Particularly preferred are sodium, potassium, and ammonium persulfates. The persulfates are generally in particulate form, have particle sizes ranging from about 0.1 to 200 microns.

The persulfates are reactive with the hydrogen peroxide or other peroxide oxidizing agent present and when the persulfate composition and aqueous oxidizing agent composition, and optionally the bleach oil composition are combined, nascent, free oxygen is generated. Without being bound by this explanation, it is believed that the typical reaction is as follows:

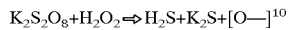

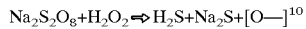

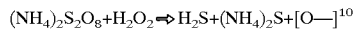

The free oxygen facilitates faster and more effective bleaching of the hair.

(2) Calculation of Active Oxygen

The active oxygen concentration in the mixture is determined by a method involving quantitation of the ferrous ions present after oxidation of the ferrous to ferric ions by the active oxygen present in the sample. The calculation of active oxygen is performed separately on each of the components used to prepare the composition, and the total alkalinity of the mixture is obtained mathematically by calculating the total alkalinity of the separate components used to prepare the mixture and considering the ratios and amounts of each of the components combined to prepare the mixture.

(i) Reagents Required:

(a) ferroin indicator (Fisher Scientific—catalog no. P-69)

(b) ceric sulfate (Fisher Scientific—catalog no. Sc 66-1, 0.1 N solution)

(c) ferrous ammonium sulfate hexahydrate—(Sigma-Aldrich—catalog no. 21,546-6) prepared by dissolving in a 1 liter volumetric flask, 157 grams of ferrous ammonium sulfate hexahydrate, 400 ml. water, and 100 ml. concentrated sulfuric acid. The flask is diluted to volume with distilled water.

(d) concentrated sulfuric acid (ii) Procedure: 0.2 grams of the mixture to be analyzed is transferred to a 250 ml. erlenmeyer flask containing 50 ml. distilled water. The mixture is shaken well to dissolve, and any lumps present crushed with a spatula. While shaking the flask 10 ml of 0.4N ferrous ammonium sulfate solution is pipetted into the flask. The flask is allowed to stand for 1 minute. Then 2.5 ml concentrated sulfuric acid and 3 drops ferroin indicator solution are added to the flask. The mixture is then titrated with 0.1N ceric sulfate until the very first permanent green coloration is seen which is a very sharp endpoint. The active oxygen present in the sample is calculated as follows:

$$\% \text{ Active Oxygen} = \frac{(a-b) \times N \times 0.8}{W}$$

wherein:

a=volume of ceric sulfate used to titrate blank in milliliters b=volume of ceric sulfate used to titrate sample in milliliters N=normality of ceric sulfate W=weight of sample in grams The mixture of the oxidizing agent composition, the bleach composition and, optionally the bleach oil composition should provide a mixture that contains 3–5% by weight of the total mixture of active oxygen as calculated according to the above method.

B. Total Alkalinity

The mixture comprises a total alkalinity concentration of about 0.7 to 1.2, preferably about 0.85 to 1.15, more preferably about 0.9 to 1.1 meq/gm. Total alkalinity is obtained by use of various alkalizing agents in the mixture. The term "alkalizing agent" means an ingredient having a pH of greater than 7, preferably about 7.5 to 11.5, more preferably about 8 to 10.5. Total alkalinity refers to the total concentration of alkalizing agents present, and includes alkalizing agents that are free to neutralize or react with other components in the composition, and bound alkalizing agents that are already reacted with other ingredients in the composition yet still contribute to the total alkalinity of the composition. For example, the preferred mixtures according to the invention contain a fatty acid of some type, generally oleic acid. The alkalizing agent such as monoethanolamine or ammonium hydroxide will react with the oleic acid to form soap (MEA-oleate or ammonium oleate). The portion of monoethanolamine that has reacted with oleic acid to form soap is no longer free to react with other ingredients in the composition and thereby does not contribute to "free alkalinity" of the mixture. A typical example of this reaction is as follows:

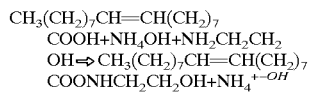

In the example above, the oleic acid has preferentially reacted with monoethanolamine to form MEA-oleate, a soap, and is thus bound. The free hydroxyl groups disassociated from the NH$_4$OH provide free alkalinity to the composition.

Generally, in order to obtain a total alkalinity concentration within the desired range, the concentration of alkalizing agents in the mixture will range from about 0.1–60%, preferably about 0.5–45%, more preferably about 1–35% by weight of the total mixture.

(1) Ingredients Contributing to Total Alkalinity (i) Ionizable Hydroxyl Compounds One type of alkalizing agent includes ionizable hydroxyl-containing compounds such as ammonium hydroxide, or alkali metal or alkaline earth metal hydroxides such as calcium, sodium, lithium, and the like. In the preferred mixtures according to the invention the alkalizing agent is a compound containing ionizable hydroxyl groups, preferably ammonium hydroxide. The ammonium hydroxide dissociates in the composition and contributes to both the free alkalinity and total alkalinity of the mixture. The free alkaline materials penetrate the hair shaft more readily and promote faster bleaching of the hair. The bound alkaline materials also contribute to the alkalinity of the composition.

(ii) Amines

Further suitable alkalizing agents include various primary, secondary, and tertiary amines such as monoethanolamine, diethanolamine, triethanolemine, and the like. If fatty acids are present in the mixture, the amines may preferentially react with them to form soap, thus binding the amines so that they do not contribute to the free alkalinity of the composition. This, in turn, permits the ionizable hydroxyl containing compounds to provide free alkalinity to the composition. Ionizable hydroxyl-containing compounds are better able to penetrate the hair shaft and promote more rapid bleaching of the hair.

(iii) Inorganic Salts

Also suitable as alkalizing agents include inorganic salts such as aluminum, sodium, potassium, and magnesium salts of inorganic or organic acids. Examples of suitable salts include alkali metal and alkaline earth metal silicates, sodium metasilicate, sodium chloride, sodium silicate, aluminum citrate, calcium saccharin, calcium salicylate, calcium citrate, calcium benzoate, magnesium acetate, magnesium ascorbate, magnesium PCA, magnesium gluconate, potassium acetate, potassium benzoate, potassium citrate, potassium sorbate, sodium acetate, sodium ascorbate, sodium silicate, sodium citrate, sodium gluconate, sodium pyruvate, and mixtures thereof. Particularly preferred inorganic sales are sodium silicate, sodium metasilicate, or mixtures thereof.

The alkalizing agents present in the composition provide a total alkalinity having the ranges specified.

(2) Calculation of Total Alkalinity

The total alkalinity of the composition comprising a mixture of the oxidizing agent composition, the persulfate composition and, if present, the bleach oil composition is determined by autotritration. Each separate component used to prepare the final mixture is assayed separately for total alkalinity concentration and the total alkalinity value of the mixture is calculated mathematically from the amounts and values of total alkalinity in the components used to prepare the final mixture.

(i) Reagents and Equipment:
  (a) Metrohm 716 DMS Titrino Autotitration System or equivalent
  (b) 150 ml. beaker
  (c) 0.1 N HCl (ii) Method:

The Metrohm 7165 DMS Titrino Autotitration System is set to "acid/base titration with pH electrode" channel. The fixed endpoint is set at pH 8.5, for free alkalinity. The final endpoint provides the total alkalinity value of the sample. The final endpoint is determined by the large point of inflection that is seen upon reaching the endpoint, usually a pH ranging from about 4 to 6.

The following equations and factors are programmed into the autitrator: Alkalinity (free or total) in terms of ml. of 0.1N HCl per gram of sample.

$$\text{Alkalinity} = \frac{V \times N}{W \times 0.1}$$

wherein:
  V=volume of 0.1N HCl used in ml.
  N=normality of 0.1N HCl, and
  W=sample weight in grams.

The sample, 0.5 grams, is weighed into a 150 ml beaker. Distilled water, 100 ml., is added and mixed well.

The titrator is started, and the amount of 0.1 N HCl required to attain pH 8.5 is noted. The titration is continued by addition of further aliquots of 0.1 N HCl in small doses until a large inflection, or decrease in pH was seen, indicating the final endpoint. The values for free alkalinity and total alkalinity are multiplied by 0.1 to obtain the results in meq/gm.

The total alkalinity of the mixture ranges from about 0.7 to 1.2 meq/gm.

C. Hydrophobic Oil

The mixture comprises about 0.5–20% by weight of the total mixture of at least one hydrophobic oil having a Hildebrand solubility parameter ($\delta$) measured in (cal/cm$^3$)$^{1/2}$ (the square root of calories per cubic centimeter), ranging from about 5 to 12. Suitable hydrophobic oils are further described below. The term "hydrophobic" means that the oil is lipophilic in character. The hydrophobic oil is preferably a liquid at room temperature (25° C.) and has a Hildebrand solubility parameter ($\delta$) value ranging from about 5 to 12, preferably about 6 to 10, more preferably about 7 to 9. The term "solubility parameter" when used in accordance with this invention means the Hildebrand solubility parameter ($\delta$) which is calculated according to the formula:

$$\delta = (\Delta Ev/V)^{1/2}$$

wherein $\Delta Ev$=heat of vaporization of the particular ingredient, and V=molecular weight/density of the ingredient.

The Hildebrand solubility parameters ($\delta$) are generally available by referring to standard chemistry textbooks or similar reference manuals. The *Journal of the Society of Cosmetic Chemistry*, Volume 36, pages 319–333, and *Cosmetics and Toiletries*, Vol. 103, October 1988, pages 47–69, both of which are hereby incorporated by reference in their entirety, list the Hildebrand solubility parameter ($\delta$) values for a wide variety of cosmetic ingredients and how the solubility parameter is calculated. Suitable hydrophobic oils which have a Hildebrand solubility parameter (δ) ranging from about 5 to 12 include coconut oil, mineral oil, isopropyl myristate, linseed oil, octyl palmitate, and so on, and those listed in the above mentioned Journal articles. Oils which have solubility parameters which are significantly less than 5 are extremely hydrophobic, and while such oils may promote preferential absorption of the active ingredients into the hair shaft by causing the water soluble actives to "repel" the oil and be preferentially pushed into the hair shaft, they are difficult to disperse in the aqueous oxidizing agent composition because of their extreme lipophilic character. Oils which have Hildebrand solubility parameters which are significantly greater than 12 are too hydrophilic and will more readily form part of the water phase of the aqueous oxidizing agent composition. Accordingly, such oils will not induce preferential absorption of the water soluble active ingredients into the hair shaft as such active ingredients are compatible with the hydrophilic ingredients present in the composition.

The mixture applied to the hair may be obtained by combining two, preferably three separate components, mixing well, and immediately applying to the hair. The mixture is capable of bleaching the hair in up to one half the time required for traditional bleach products. Generally, traditional bleaches require about 20 to 60 minutes to lighten hair. The claimed mixture is capable of providing the same degree of lightening to the hair in 10 to 45 minutes, preferably 10 to 30 minutes.

II. The Hair Bleach Components

The preferred hair bleach composition is prepared by combining two, optionally three components, which will be further described herein. The first component is an aqueous oxidizing agent composition. The second component is a persulfate composition. The third, optional, component is a bleach oil composition. The individual components will contain the ingredients required to provide a mixture having the active oxygen concentration, total alkalinity, and hydrophobic oil concentrations that are necessary to achieve optimal bleaching of the hair.

A. The Persulfate Composition

The persulfate composition generally comprises a mixture of persulfate compounds which are capable of bleaching the hair, particulate fillers, and, if desired, inorganic particulate colorants. The persulfate composition may be found in the powdered particulate form, or in the form of a cream or paste as described in U.S. Pat. No. 5,888,484; and U.S. patent application Ser. No. 09/774,890, filed Feb. 1, 2001, assigned to Revlon Consumer Products Corporation, naming Teresita Imperial as inventor, both of which are hereby incorporated by reference in their entirety.

1. Persulfates

The persulfate composition comprises about 15–65%, preferably about 20–60%, more preferably about 25–55% by weight of the total persulfate composition of one or more inorganic persulfates which may be alkali metal or alkaline earth metal persulfates, or ammonium persulfate.

2. Alkalizing Agents

The persulfate composition preferably contains one or more alkalizing agents. Preferred alkalizing agents are one or more inorganic salts as set forth herein. Suggested ranges of inorganic salts are from about 0.1–40%, preferably about 0.5–35%, preferably about 1–30% by weight of the total composition.

3. Particulate Fillers

The persulfate composition also preferably comprises one or more particulate fillers. Preferably, the persulfate composition comprises about 5–60%, preferably about 8–55%, more preferably about 10–50% by weight of the total persulfate composition of the particulate fillers. The term "particulate filler" means a generally inert particulate having a particle size of about 0.1–250 microns. The particulate fillers provide volume and, when mixed with the persulfates, dilute the persulfate particles. A variety of particulate fillers are suitable including inorganics, inorganic salts, hydrophilic colloids, carbohydrates, soaps, alkyl sulfates, and the like.

(a) Inorganics

Examples of inorganics include silica, hydrated silica, alumina, attapulgite, bentonite, calcium oxide, chalk, diamond powder, diatomaceous earth, fuller's earth, hectorite, kaolin, mica, magnesium oxide, magnesium peroxide, montmorillonite, pumice, talc, tin oxide, zeolite, zinc oxide, and the like.

(b) Hydrophilic Colloids

Examples of suitable hydrophilic colloids include hydroxyethylcellulose, locust bean gum, maltodextrin, methylcellulose, agar, dextran, dextran sulfate, gelatin, pectin, potassium alginate, sodium carboxymethylchitin, xanthan gum, and the like.

(c) Carbohydrates

Examples of suitable carbohydrates include sugars such as glucose, sucrose, maltose, xylose, trehelose, and derivatives thereof, in particular sugar esters of long chain, $C_{14-30}$ fatty acids, as well as dextrins, cellulosics, and derivatives thereof.

(d) Soaps and Alkyl Sulfates

Examples of soaps and alkyl sulfate particles that may act as particulate fillers include the aluminum, sodium, and potassium salts of fatty acids such as aluminum distearate, aluminum isostearate, aluminum myristate, calcium behenate, calcium stearate, calcium behenate, magnesium stearate, magnesium tallowate, potassium palmitate, potassium stearate, potassium oleate, sodium stearate, sodium oleate, sodium myristate, sodium palmitate, and the like. Suitable alkyl sulfates include sodium lauryl sulfate, sodium cetyl sulfate, sodium myristyl sulfate, sodium octyl sulfate, and the like.

4. Inorganic Colorants

If desired, the persulfate composition may comprise about 0.01–2%, preferably about 0.05–1%, more preferably about 0.1–1% by weight of the total persulfate composition of an inorganic colorant. The inorganic colorant is preferably in the particulate form and will provide a subtle coloration to the powder composition to make it more aesthetically pleasing for commercial purposes. Particularly preferred for use in the bleach composition is ultramarine blue.

5. Hydrophobic Oil

It may be desirable to include the hydrophobic oil in the persulfate composition. If so, the hydrophobic oil must be present in an amount sufficient to provide a mixture having a concentration ranging from about 0.5 to 20% by weight of the total mixture of the hydrophobic oil. The suitable hydrophobic oils are those discussed above with respect to the mixture. If present in the persulfate composition, suggested ranges of hydrophobic oil are from about 0.1–70%, preferably about 0.5–60%, more preferably about 1–50% by weight of the total composition.

6. Other Lipophilic Ingredients

It may be desirable to include one or more oils, or lipophilic ingredients, other than the hydrophobic oil in the persulfate composition. Suitable oils are lipophilic ingredients that may be liquids, solids, or semi-solids at room temperature (25° C.) which have Hildebrand solubility parameters which are less than 5 or greater than 12. Examples of such lipophilic materials include short chain hydrocarbons, polar hydrophilic oils, fatty acids, fatty alcohols, silicone waxes, and so on. If present the other lipophilic ingredients may be found in the composition ranging from about 0.1–50%, preferably about 0.5–40%, preferably about 1–35% by weight of the total composition.

B. The Aqueous Oxidizing Agent Composition.

The aqueous oxidizing agent composition may be in the solution or emulsion form. If the latter, the emulsion may be in the water-in-oil or oil-in-water form. Further, the emulsion may also be in the microemulsion form, if desired.

When the aqueous oxidizing agent is in the solution form the composition preferably comprises about 1–30% by weight of the total composition of an oxidizing agent, preferably hydrogen peroxide, and about 70–99% by weight of the total composition of water. Other water soluble ingredients may be included in the solution, such as humectants, preservatives, water soluble thickeners, antioxidants, and so on.

When the aqueous oxidizing agent composition is in the emulsion form, the composition preferably comprises about 1–30% of oxidizing agent, preferably hydrogen peroxide, about 50–99% water, and about and 0.01–30%, preferably about 0.05–20%, more preferably about 0.1–15% of an oily phase. The aqueous oxidizing agent composition may be in the form of a water-in-oil or oil-in-water emulsion or in the form of a transparent microemulsion wherein the dispersed particles in the continuous phase are so small (generally about 5–1500 Å) that the composition is optically clear. Examples of suitable microemulsion compositions are set froth in U.S. Pat. No. 6,315,989, which is hereby incorporated by reference in its entirety. It is also suitable that the aqueous oxidizing agent composition be in the form of a composition containing liquid crystals as set forth in U.S. Pat. No. 6,238,653, which is hereby incorporated by reference in its entirety.

The various ingredients that may be found in the aqueous oxidizing agent composition (also referred to as "developer") are as follows.

1. Oxidizing Agent.

Preferably the oxidizing agent is hydrogen peroxide, although other suitable peroxides such as urea peroxide, sodium perborate, etc. may be used as well. Preferably the aqueous oxidizing agent composition contains hydrogen peroxide. The oxidizing agent contributes to formation of active oxygen when the various components are combined.

2. Hydrophobic Oil

The hydrophobic oil may be present in the aqueous oxidizing agent composition if this composition is in the emulsion form. If so, suggested ranges are about 1–85%, preferably about 3–70%, preferably about 5–65% by weight of the total composition. The hydrophobic oils that are suitable are as set forth herein.

3. Other Oils

If the aqueous oxidizing agent is in the form of an emulsion, the composition may comprise one or more oily or lipophilic ingredients either alone or in combination with the hydrophobic oil. Suitable lipophilic ingredients may be liquids, semi-solids, or solids oils at room temperature (25° C.) which have Hildebrand solubility parameters (δ) which are less than 5 or greater than 12. Examples of such lipophilic materials include short chain hydrocarbons, polar hydrophilic oils, fatty acids, fatty alcohols, silicone waxes, and so on. If such other lipophilic ingredients are present, suggested ranges are about 0.1–50%, preferably about 0.5–35%, more preferably about 1–30% by weight of the total composition.

4. Humectants

Humectants may be present in the aqueous oxidizing agent composition. If so, suggested ranges are from about 0.01–10%, more preferably about 0.05–8%, most preferably about 0.1–5% by weight of the total composition of humectant. Suitable humectants include monomeric, homopolymeric, and/or block copolymeric ethers as well as mono-, di-, or polyhydric alcohols.

Suitable ethers are formed by the polymerization of monomeric alkylene oxides, generally ethylene or propylene oxide. Such polymeric ethers have the following general formula:

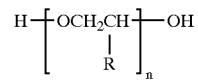

wherein R is H or lower alkyl and n is the number of repeating monomer units, and ranges from 1 to 500.

Also suitable are polyols such as glycerine or $C_{1-4}$ alkylene glycols and the like. Particularly preferred are $C_{1-4}$ alkylene glycols, in particular propylene and/or butylene glycol and ethoxydiglycol.

Suitable mono-, di-, or polyhydric alcohols include glycerin, butylene glycol, ethylene glycol, propylene glycol, and so on.

5. Water Soluble Thickeners

The aqueous oxidizing agent composition may contain one or more water soluble thickeners. If present suggested ranges are from about 0.1–25%, preferably about 0.5–20%, more preferably 1–15% by weight of the total composition. Suitable thickeners include (a) Acrylic Copolymer Thickeners Suitable acrylic copolymeric thickeners are comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof. Preferably, the A monomer comprises one or more of acrylic acid or methacrylic acid, and the B monomer comprises is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer, with the remainder water. Preferably, the thickening agent is a polymer comprised of A, B, and C monomers wherein A and B are as defined above, and C has the general formula:

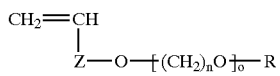

Preferably, in the copolymer used for the secondary thickening agent in the preferred embodiment of the invention, A and B are as above defined; and in the C monomer Z is $(CH_2)_m$, m is 1–2, n is 2, and o is 2–100, and R is a $C_{12-22}$ straight or branched chain alkyl. More preferably in the C monomer m is 1, n is 2, o is 10, and R is $C_{18}$ or stearyl, and the compound is steareth-10 allyl ether/acrylate copolymer, which may be purchased from Allied Colloids under the tradename Salcare SC90.

Also suitable is an aqueous solution of an acrylic polymer comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof. Preferably, the A monomer comprises one or more of acrylic acid or methacrylic acid, and the B monomer comprises is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer, with the remainder water. The composition of the acrylic copolymer may contain from about 0.1–99 parts of the A monomer, and about 0.1–99 parts of the B monomer. Preferably, the acrylic copolymer contains enough of the A monomer to enable ionization in a basic solution, thereby causing the ionized carboxylic acid groups in the polymer to repel each other, and thereby "swallow" water. Particularly preferred acrylic copolymer solutions suitable for use in the developer composition include those sold by Seppic, Inc., under the tradename Capigel, in particular, Capigel 98, which is a white liquid having a pH of 2 to 4, a solids content of about 29–31, a density of 1.04 to 1.08, and a viscosity of 700–1000 millipascal seconds at 25° C.

(b) Associative Thickeners

Various other types of associative thickeners may be present, including water soluble urethane homo- and copolymers, and the like.

6. Nonionic Surfactants

If desired, the aqueous developer composition may contain one or more nonionic surfactants. Recommended ranges are 0.01–10%, preferably 0.05–8%, more preferably 0.1–7% by weight of the total composition.

(a) Alkoxylated Alcohols

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5-30, which is formed by the reaction of behenyl alcohol and ethylene oxide where the number of repeated ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. Particularly preferred is Ceteareth 20, which is the reaction product of a mixture of cetyl and stearyl alcohol with ethylene oxide, and the number of repeating ethylene oxide units in the molecule is 20.

(b) Alkoxylated Carboxylic Acids

Also suitable as the nonionic surfactant are alkyoxylated carboxylic acids, which are formed by the reaction of a carboxylic acid with an alkylene oxide or with a polymeric ether. The resulting products have the general formula:

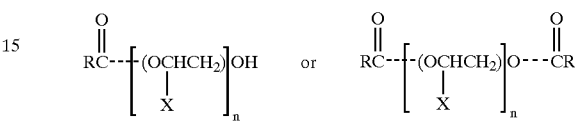

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

(c) Sorbitan Derivatives

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

The aqueous oxidizing agent composition may also comprise a variety of other ingredients including cationic, amphoteric, or zwitterionic surfactants, preservatives.

C. The Bleach Oil Composition

The third component that may be used to prepare the mixture applied to hair, is a bleach oil composition. The term "bleach oil composition" means a liquid composition that is mixed with the aqueous oxidizing agent composition and the persulfate composition to provide a mixture suitable for bleaching hair. Generally the bleach oil composition will contain one or more ingredients that are capable of conditioning hair and ameliorating the drying effects that bleaches sometimes have on hair. In the preferred embodiment of the invention the mixture that is applied to hair is obtained by combining an aqueous oxidizing agent composition, a persulfate composition, and a bleach oil composition. In the preferred embodiment, the hydrophobic oil is preferably present as part of the bleach oil composition rather than in the aqueous oxidizing agent composition.

The bleach oil composition is preferably in the emulsion form, and may be a water-in-oil or oil-in-water emulsion or microemulsion. The bleach oil composition generally comprises about 1–75%, preferably about 2–70%, more preferably about 5–65% by weight of the total composition of water, and about 0.1–50%, preferably about 0.5–45%, more preferably about 1–40% by weight of the total composition of hydrophobic oil. The hydrophobic oils are as mentioned above with respect to the aqueous oxidizing agent composition. In addition, the bleach oil composition may comprise other ingredients such as surfactants, alkalizing agents, antioxidants, humectants, other lipophilic ingredients, all in the amounts taught above with respect to the aqueous oxidizing agent composition. Additionally, the bleach oil may be found in the microemulsion form wherein the dispersed particles in the emulsion exhibit a small particle size, e.g. from about 5 to 1500 Å.

The preferred bleach oil composition contains at least one alkalizing agent that is capable of contributing to the total alkalinity of the mixture. Suggested ranges of alkalizing agent found in the bleach oil are about 0.1–50%, preferably about 0.5–45%, more preferably about 1–40% by weight of the total composition. Preferred is where the bleach oil contains an ionizable hydroxyl containing compound as the alkalizing agent.

III. The Method

The oxidizing agent composition and the persulfate composition and, optionally, the bleach oil composition are combined in sufficient ratios to yield a final mixture that comprises an active oxygen concentration of about 3 to 5% by weight of the total composition, a total alkalinity concentration of about 0.7–1.2 meq/gm., and 0.5–20% by weight of the total mixture of an oil having a Hildebrand solubility parameter of 5–12. Generally, determination of suitable ratios of each of the two or three components is well within the skilled artisan's capabilities. Generally, in the preferred embodiment of the invention, the mixture comprises about 20–80% by weight of the total mixture of the aqueous oxidizing agent composition, about 5–40% by weight of the total mixture of persulfate composition, and, optionally, about 5–30% by weight of the total mixture of the bleach oil composition.

The invention will be further described in connection with the following examples, that are set forth for the purposes of illustration only.

EXAMPLE 1

An aqueous oxidizing agent composition (or developer) was made according to the following formula:

|  | w/w % |
|---|---|
| Water | 68.91 |
| EDTA | 0.02 |
| Laureth 23 | 1.50 |
| Cetearyl alcohol | 1.35 |
| Sodium lauryl sulfate | 0.075 |
| Sodium cetearyl sulfate | 0.075 |
| Cetearyl alcohol | 1.00 |
| Hydrogen peroxide (35% aqueous solution) | 26.00 |
| Phosphoric acid | 0.02 |
| Disodium phosphate | 0.05 |
| Steareth-10 allyl ether/acrylates copolymer | 1.00 |

A powdered persulfate composition was made according to the following formula:

|  | w/w % |
|---|---|
| Potassium persulfate | 40.00 |
| Sodium persulfate | 10.00 |
| Ammonium persulfate | 15.00 |
| Sodium silicate | 20.00 |
| Hydrated silica | 1.00 |
| Sodium lauryl sulfate | 2.75 |
| Tetrasodium EDTA | 1.25 |
| Sodium metasilicate | 7.00 |
| Hydroxyethylcellulose | 2.00 |
| Xanthan gum | 1.00 |

A bleach oil composition made according to the following formula:

|  | w/w % |
|---|---|
| Water | 20.60 |
| Tetrasodium EDTA | 0.80 |
| Isopropanol amine | 10.00 |
| Ethoxydiglycol | 8.00 |
| Laureth 4 | 15.00 |
| Oleic acid | 13.00 |
| Ethanolamine | 3.00 |
| Isopropyl myristate | 9.50 |
| Coconut oil | 5.00 |
| Ammonium hydroxide | 13.00 |
| Fragrance | 1.00 |
| Hydrolyzed marine collagen | 0.50 |
| Wheat amino acids | 0.50 |
| Sodium benzotriazolyl sulfonate/buteth 3/ Tributyl citrate | 0.10 |

The mixture to be applied to hair was prepared by combining 28.5 grams bleach oil, 123.5 grams of the aqueous oxidizing agent composition, and 47.5 grams of the persulfate composition and mixing well. The composition had an active oxygen concentration of 3.52% by weight of the total mixture, a total alkalinity concentration of 0.955 meq/gm, and the amount of hydrophobic oil in the mixture was 2% by weight of the total mixture.

The mixture was used to dye light brown virgin hair swatches weighing about 1.5 grams per swatch. The mixture was applied to the swatches, and the color measured at 10 minutes and 30 minutes using the datacolor color tools QC (version 1.2.1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results were as follows:

| Time (minutes) | L | a | b |
|---|---|---|---|
| 10 | 45.50 | 9.40 | 23.49 |
| 30 | 57.77 | 9.40 | 29.04 |

EXAMPLE 2

Comparative bleach oil compositions were prepared as follows:

|  | Sample | | | | | | | | |
|---|---|---|---|---|---|---|---|---|---|
|  | 1 | 2 | 3 | 4 | 5 | 6 | 7 | 8 | 9 |
| Water | 20.6 | 35.1 | 20.6 | 20.6 | 20.6 | 20.6 | 20.6 | 20.6 | 20.6 |
| Tetrasodium EDTA | 0.8 | 0.8 | 0.8 | 0.8 | 0.8 | 0.8 | 0.8 | 0.8 | 0.8 |
| Isopropanolamine | 10.0 | 10.0 | 10.0 | 10.0 | 10.0 | 10.0 | 10.0 | 10.0 | 10.0 |
| Ethoxydiglycol | 8.0 | 8.0 | 8.0 | 8.0 | 8.0 | 8.0 | 8.0 | 8.0 | 8.0 |
| Laureth-4 | 15.0 | 15.0 | 15.0 | 15.0 | 24.5 | 24.5 | 15.0 | 15.0 | 15.0 |
| Oleic acid | 13.0 | 13.0 | 13.0 | 13.0 | 13.0 | 13.0 | 13.0 | 13.0 | 13.0 |
| Ethanolamine | 3.0 | 3.0 | 3.0 | 3.0 | 3.0 | 3.0 | 3.0 | 3.0 | 3.0 |
| Isopropyl myristate | 9.5 | — | — | 14.5 | — | — | — | — | — |
| Coconut oil | 5.0 | — | — | — | 5.0 | — | — | — | — |
| Mineral Oil | — | — | — | — | — | 5.0 | — | — | — |
| Oleyl alcohol | — | — | — | — | — | — | — | 14.5 | — |
| Triacetin | — | — | — | — | — | — | — | — | 14.50 |
| Benzyl alcohol | — | — | — | — | — | — | 14.5 | — | — |
| Propylene glycol | — | — | 14.5 | — | — | — | — | — | — |
| Ammonium hydroxide | 13.0 | 13.0 | 13.0 | 13.0 | 13.0 | 13.0 | 13.0 | 13.0 | 13.0 |
| Fragrance | 1.0 | 1.0 | 1.0 | 1.0 | 1.0 | 1.0 | 1.0 | 1.0 | 1.0 |
| Hydrolyzed collagen* | 0.5 | 0.5 | 0.5 | 0.5 | 0.5 | 0.5 | 0.5 | 0.5 | 0.5 |
| Wheat amino acids | 0.5 | 0.5 | 0.5 | 0.5 | 0.5 | 0.5 | 0.5 | 0.5 | 0.5 |
| UV absorber** | 0.1 | 0.1 | 0.1 | 0.1 | 0.1 | 0.1 | 0.1 | 0.1 | 0.1 |

*hydrolyzed marine collagen
**sodium benzotriazolyl sulfonate/buteth-3/tributyl citrate The above compositions were combined with the powdered persulfate composition and aqueous oxidizing agent composition set forth in Example 1 in the following ratios: 28.5 grams bleach oil, 123.5 grams aqueous oxidizing agent composition, and 47.5 powdered persulfate composition. Light brown virgin hair swatches (1.5 grams per swatch), were colored using the compositions and the chromaticity of the swatches was measured at 10 and 30 minutes in accordance with the equipment and methods mentioned in Example 1.

|  | Sample | | | | | | | | | |
|---|---|---|---|---|---|---|---|---|---|---|
|  | L (10') | L (30') | $\Delta$L (10') | $\Delta$L (30') | $\Delta$E (10') | $\Delta$E (30') | a (10') | a (30') | b (10') | b (30') |
| 1 | 45.50 | 57.77 |  |  |  |  | 9.40 | 9.40 | 23.49 | 29.04 |
| 2 | 43.75 | 54.45 | −1.74 | −3.32 | 1.98 | 3.67 | 9.66 | 9.74 | 22.57 | 27.50 |
| 3 | 44.07 | 52.98 | −1.42 | −4.79 | 1.58 | 4.98 | 9.57 | 10.06 | 22.81 | 27.84 |
| 4 | 44.38 | 58.42 | −1.11 | 0.66 | 2.04 | 1.51 | 9.24 | 8.62 | 21.79 | 27.93 |
| 5 | 44.66 | 57.63 | −0.83 | −0.14 | 2.13 | 0.81 | 9.12 | 8.99 | 21.54 | 28.36 |
| 6 | 46.39 | 57.38 | 0.89 | −0.38 | 1.03 | 1.62 | 9.34 | 9.01 | 22.98 | 27.51 |
| 7 | 44.08 | 54.97 | −1.42 | −2.80 | 1.52 | 3.04 | 9.50 | 9.51 | 22.93 | 27.87 |
| 8 | 44.54 | 56.08 | −0.96 | −1.69 | 1.15 | 1.72 | 9.44 | 9.72 | 22.86 | 28.89 |
| 9 | 44.07 | 55.49 | −1.43 | −2.27 | 1.81 | 2.37 | 9.16 | 9.43 | 22.41 | 28.39 | wherein $\Delta$L=the difference in lightening between sample 1 and comparative samples 2–9 in 10 and 30 minutes, L (10') and L(30'); and $\Delta$E=the difference in overall color change between sample 1 and comparative samples 2–9 in 10 and 30 minutes. The $\Delta$E was calculated as follows:

$$\Delta E = (L-L_o)^2 + (a-a_o)^2 + (b-b_o)^2$$

wherein L is the is the level of darkness or lightness, a is the red and green components, and b is yellow and blue components, and wherein the subscript o means prior to dyeing.

The solubility parameter δ in (cal/cm³)^(1/2) for the oils used in samples 1–9 are referenced below:

| Oil | δ |
| --- | --- |
| Mineral oil | 7.09 |
| Isopropyl myristate | 8.02 |
| Oleyl alcohol | 8.95 |
| Triacetin | 10.77 |
| Benzyl alcohol | 12.31 |

| Oil | δ |
| --- | --- |
| Propylene glycol | 14.00 |
| Water | 23.40 |
| Coconut oil | 8.1 |

Samples 2, 3, and 7 do not contain a hydrophobic oil having a δ ranging from about 5 to 12 (cal/cm³)^(1/2). Accordingly, it is seen that when the hydrophobic oil is not present the hair swatches exhibit inferior lightening when compared to the compositions where a hydrophobic oil having a δ ranging from about 5 to 12 is present.

EXAMPLE 3

The mixture of the aqueous oxidizing agent composition, the persulfate composition, and the bleach oil composition set forth Example 1 was compared with mixtures obtained by combining the aqueous oxidizing agent composition and persulfate composition of Example 1 with the bleach oil composition found in various competitive products. The total alkalinity, active oxygen, and hydrophobic oil concentration of the mixtures was calculated.

| | MIXTURE | | | | | | | |
| --- | --- | --- | --- | --- | --- | --- | --- | --- |
| Bleach Oil | 1 | 2 | 3 | 4 | 5 | 6 | 7 | 8 |
| Total alkalinity (meq/g) | 2.143 | 1.237 | 2.72 | 0.95 | 1.34 | 0.86 | 0.647 | 2.043 |
| Free alkalinity meq/gml | 1.277 | 0.375 | 2.360 | 0.500 | 0.820 | 0.320 | 0.196 | 1.135 |
| Aqueous oxidizing agent | 1 | 1 | 1 | 1 | 1 | 1 | 1 | 1 |
| Active oxygen (%) | 4.23 | 4.23 | 4.23 | 4.23 | 4.23 | 4.23 | 4.23 | 4.23 |
| Persulfate | 1 | 1 | 1 | 1 | 1 | 1 | 1 | 1 |
| Total alkalinity (meq/gm) | 2.724 | 2.724 | 2.724 | 2.724 | 2.724 | 2.724 | 2.724 | 2.724 |
| Free alkalinity (meq/gm) | 2.191 | 2.191 | 2.191 | 2.191 | 2.191 | 2.191 | 2.191 | 2.191 |
| Mixture of: | 1 + 1 + 1 | 2 + 1 + 1 | 3 + 1 + 1 | 4 + 1 + 1 | 5 + 1 + 1 | 6 + 1 + 1 | 7 + 1 + 1 | 8 + 1 + 1 |
| Total Alkalinity (meq/gm) | 0.955 | 0.825 | 1.037 | 0.784 | 0.840 | 0.771 | 0.741 | 0.940 |
| Free Alkalinity (meq/gm) | 0.704 | 0.575 | 0.859 | 0.593 | 0.639 | 0.567 | 0.550 | 0.684 |
| Active Oxygen (% by weight of mixture) | 3.52 | 3.52 | 3.52 | 3.52 | 3.52 | 3.52 | 3.52 | 3.52 |

*Mixture:

1. 123.5 grams aqueous oxidizing agent composition of Example 1 + 47.5 grams of persulfate composition of Example 1 + 28.5 grams of bleach oil composition of Example 1.
2. 123.5 grams aqueous oxidizing agent composition of Example 1 + 47.5 grams of persulfate composition of Example 1 + 28.5 grams of Clairol Maxi Blonde Bleach oil, the ingredient labeling on the product identifying the composition as containing: oleic acid, SD alcohol 40, water, PEG-5 soyamine, ethyl hydroxymethyl oleyl oxazoline, nonyl nonoxynol 49, trideceth-6, ethoxydiglycol, ammonium hydroxide, fragrance, EDTA, D&C Violet No. 2, D&C Green No. 6.
3. 123.5 grams aqueous oxidizing agent composition of Example 1 + 47.5 grams of persulfate composition of Example 1 + 28.5 grams Herbal Essences Bleach Blonding oil, the ingredient labeling on the product identifying the composition as containing: water, ethanolamine, propyleneglycol, soytrimonium chloride, C12–15 pareth-3, oleic acid, ethoxydiglycol, steareth-21, fragrance, oleamide MIPA, *crataegus monogina* fruit extract, *spiraea ulmaria* flower extract, *anthemis nobilis* flower extract, tocopheryl acetate, *magnolia acuminata* bark extract, cocamidopropyl betaine, C11–15 pareth-9, hydrolyzed vegetable protein, PEG-150/stearyl/SMDI copolymer, erythrobic acid, EDTA, sodium sulfite, sodium metasilicate, Polysorbate 20.
4. 123.5 grams aqueous oxidizing agent composition of Example 1 + 47.5 grams of persulfate composition of Example 1 + 28.5 grams Feria 200 Blonding oil, the ingredient labeling on the product identifying the composition as containing: deceth-3, deceth-5, water, oleic acid, propyleneglycol, oleth-30, ammonium hydroxide, butoxydiglycol, oleyl alcohol, fragrance.
5. 123.5 grams aqueous oxidizing agent composition of Example 1 + 47.5 grams of persulfate composition of Example 1 + 28.5 grams Feria 205 Blonding oil, the ingredient labeling on the product identifying the composition as containing: water, cetearyl alcohol, propyleneglycol, deceth-3, laureth-12, ammonium hydroxide, oleth-30, lauric acid, glycol distearate, polyquaternium-22, ethanolamine, silica dimethyl silylate, pentasodium pentetate, carbomer, fragrance.
6. 123.5 grams aqueous oxidizing agent composition of Example 1 + 47.5 grams of persulfate composition of Example 1 + 28.5 grams of Frost and Glow blonding oil, the ingredient labeling on the product identifying the composition as containing: MEA-oleate, water, isopropyl myristate, laureth-4, isopropyl alcohol, ethoxydiglycol, oleyl alcohol, ethanolamine, *simmondsia chinensis* (jojoba) seed oil, fragrance, tetrasodium EDTA.
7. 123.5 grams aqueous oxidizing agent composition of Example 1 + 47.5 grams of persulfate composition of Example 1 + 28.5 grams of Garnier Nutrisse Lightening Kit bleach oil, the ingredient labeling on the product identifying the composition as containing: deceth-3, deceth-5, water, oleic acid, propyleneglycol, oleth-30, ammonium hydroxide, butoxydiglycol, oleyl alcohol, fragrance.
8. 123.5 grams aqueous oxidizing agent composition of Example 1 + 47.5 grams of persulfate composition of Example 1 + 28.5 grams of Clairol XtremeFX Industrial Blonde bleach oil, the ingredient labeling on the product identifying the composition as containing: oleic acid, oleth-2, water, propyleneglycol, ethanolamine, isopropyl alcohol, soytrimonium chloride, ethoxydiglycol, C12–15 pareth-3, hexyleneglycol, ammonium hydroxide, fragrance, erythorbic acid, sodium sulfate, EDTA.

The above mixtures were used to dye light brown virgin hair swatches weighing about 1.5 grams per swatch. The mixtures were applied to the swatches, and the color measured at 10 minutes and 30 minutes using the datacolor color tools QC (version 1.2.1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results were as follows: accordance with the equipment and methods mentioned in Example 1.

| Mixture | L (10') | L (30') | ΔL (10') | ΔL (30') | ΔE (10') | ΔE (30') | a (10') | a (30') | b (10') | b (30') |
|---|---|---|---|---|---|---|---|---|---|---|
| 1 + 1 + 1 | 45.5 | 57.7 | | | | | 9.40 | 9.40 | 23.49 | 29.04 |
| 2 + 1 + 1 | 43.68 | 54.51 | −1.81 | −3.26 | 2.78 | 3.46 | 9.19 | 9.38 | 21.39 | 27.88 |
| 3 + 1 + 1 | 43.52 | 54.62 | −0.20 | −3.14 | 2.66 | 3.34 | 9.22 | 9.59 | 21.73 | 27.94 |
| 4 + 1 + 1 | 43.22 | 54.51 | −2.27 | −3.26 | 2.77 | 3.46 | 9.33 | 9.38 | 21.91 | 27.88 |
| 5 + 1 + 1 | 44.84 | 56.89 | −0.66 | −0.88 | 1.35 | 1.06 | 9.39 | 9.52 | 22.31 | 28.47 |
| 6 + 1 + 1 | 42.26 | 54.89 | −3.23 | −2.88 | 4.19 | 3.18 | 9.12 | 9.58 | 20.85 | 27.69 |
| 7 + 1 + 1 | 45.56 | 56.43 | 0.34 | −1.34 | 0.90 | 1.86 | 9.49 | 9.19 | 22.66 | 27.77 |
| 8 + 1 + 1 | 44.45 | 54.90 | −0.11 | −2.87 | 2.04 | 3.41 | 9.02 | 9.08 | 23.57 | 27.23 |

The above results illustrate that the claimed mixture, containing a hydrophobic oil and the active oxygen and total alkalinity concentration within the claimed ranges, provides a bleach composition that provides improved lightening to hair in 30 minutes when compared to the other products.

EXAMPLE 4

An aqueous oxidizing agent composition (or developer) was made according to the following formula:

| | w/w % |
|---|---|
| Water | 67.41 |
| EDTA | 0.02 |
| Isopropyl alcohol | 2.00 |
| Laureth 23 | 2.00 |
| Cetearyl alcohol, Sodium Lauryl Sulfate, Sodium cetearyl sulfate(90:5:5) | 1.50 |
| Cetearyl alcohol | 1.00 |
| Hydrogen peroxide (35% aqueous solution) | 26.00 |
| Phosphoric acid | 0.02 |
| Disodium phosphate | 0.05 |

A powdered persulfate composition was made according to the following formula:

| | w/w % |
|---|---|
| Potassium persulfate | 45.00 |
| Sodium persulfate | 10.00 |
| Ammonium persulfate | 10.00 |
| Sodium silicate | 20.00 |
| Hydrated silica | 0.80 |
| Sodium lauryl sulfate | 3.45 |
| Tetrasodium EDTA | 1.50 |
| Sodium Metasilicate | 7.25 |
| Hydroxyethylcellulose | 2.00 |

A bleach oil composition made according to the following formula:

| | w/w % |
|---|---|
| Water | 21.70 |
| Tetrasodium EDTA | 0.80 |
| Isopropanolamine | 10.00 |
| Ethoxydiglycol | 8.00 |
| Laureth-4 | 15.00 |
| Oleic acid | 12.50 |
| Ethanolamine | 3.00 |

-continued

| | w/w % |
|---|---|
| Isopropyl myristate | 15.00 |
| Ammonium hydroxide | 13.00 |
| Fragrance | 1.00 |

The mixture to be applied to hair was prepared by combining 30 grams bleach oil, 120 grams of the aqueous oxidizing agent composition, and 60 grams of the persulfate composition and mixing well.

Half head tests were conducted on models with brown hair. The above mixture was applied to one half of the models' heads. The mixture was left on the hair for 15 minutes, then removed by rinsing well with water.

Then Feria 200, combined according to package instructions, was applied to the other, untreated half of the model's head. The ingredient labeling for the components of the Feria 200 product is reproduced below:

Aqueous Oxidizing Agent Composition (developer): water, hydrogen peroxide, cetearyl alcohol, trideceth-2 carboxamide MEA, ceteareth-30, glycerin, pentasodium pentetate, sodium stannate, tetrasodium pyrophosphate.

Powdered Persulfate Composition: potassium persulfate, sodium persulfate, ammonium chloride, sodium metasilicate, sodium silicate, water, EDTA, hydrated silica, sodium lauryl sulfate.

Bleach Oil Composition: deceth-3, deceth-5, water, oleic acid, propylene glycol, oleth-30, ammonium hydroxide, butoxydiglycol, oleyl alcohol, fragrance.

The Feria 200 mixture was left on the models' heads for 30 minutes, then removed by rinsing well with water. The two sides were visually compared by an experienced hair color technician. It was noted that the side treated with the mixture of Example 4 after 15 minutes exhibited the same degree and nature of lightening as the side treated with Feria 200 after 30 minutes. Accordingly, the mixture of claim 4 provided the same degree of lightening in one half the time.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An emulsion hair bleach composition prepared by combining (i) an aqueous oxidizing agent composition, and (ii) a persulfate composition comprising an organic oil having a Hildebrand solubility parameter of 5–12 $(cal/cm^3)^{1/2}$, and in amounts sufficient to provide a mixture containing:
(a) an active oxygen concentration of about 3 to 5% by weight of the total mixture,
(b) a total alkalinity concentration of about 0.7–1.2 meq/gm., and
(c) about 0.5–20% by weight of the total mixture of an oil having a Hildebrand solubility parameter of 5–12 $(cal/cm^3)^{1/2}$.

2. The mixture of claim 1 wherein the active oxygen is provided by one or more of peroxide oxidizing agents or persulfates.

3. The mixture of claim 2 wherein the peroxide oxidizing agent is hydrogen peroxide.

4. The mixture of claim 2 wherein the persulfate is selected from the group consisting of alkaline earth metal persulfate, alkali metal persulfate, ammonium persulfate, and mixtures thereof.

5. The mixture of claim 1 wherein the active oxygen concentration is about 3.2 to 4.8% by weight of the total mixture.

6. The mixture of claim 1 wherein the total alkalinity is provided by one or more alkalizing agents.

7. The mixture of claim 6 wherein the alkalizing agents either alone or in combination have a pH ranging from about 7.5 to about 11.5.

8. The mixture of claim 7 wherein the alkalizing agent is selected from the group consisting of ionizable hydroxyl containing compound, amine, inorganic salt, and mixtures thereof.

9. The mixture of claim 8 wherein the ionizable hydroxyl containing compound is selected from the group consisting of ammonium hydroxide, sodium hydroxide, potassium hydroxide, and mixtures thereof.

10. The mixture of claim 8 wherein the amine is a primary amine.

11. The mixture of claim 10 wherein the amine is a $C_{1-10}$ alkanolamine.

12. The mixture of claim 11 wherein the alkanolamine is monoethanolamine.

13. The mixture of claim 8 wherein the inorganic salt is selected from the group consisting of alkali metal silicate, alkaline earth metal silicate and mixtures thereof.

14. The mixture of claim 1 wherein the total alkalinity includes alkalizing agents that are free to neutralize with other components in the composition and bound alkalizing agents that are already reacted wit other ingredients in the composition.

15. The mixture of claim 1 wherein the organic oil has a Hildebrand solubility parameter ranging from about 7 to about 9 $(cal/cm^3)^{1/2}$.

16. The mixture of claim 1 wherein the organic oil having Hildebrand solubility parameter of 5–12 $(cal/cm^3)^{1/2}$ is selected from the group consisting of coconut oil, mineral oil, isopropyl myristate, linseed oil, octyl palmitate, and mixtures thereof.

17. The mixture of claim 1 which is prepared by combining an aqueous oxidizing agent composition, a persulfate composition, and a bleach oil composition.

18. The mixture of claim 17 wherein the aqueous oxidizing agent composition is a solution or emulsion of hydrogen peroxide.

19. The mixture of claim 18 wherein the aqueous oxidizing agent composition is an emulsion.

20. The mixture of claim 18 wherein the aqueous oxidizing agent composition comprises, by weight of the total composition:
about 1–30% hydrogen peroxide,
about 50–99% water, and
about 0.1–30% by weight of the total composition of an oily phase.

21. The mixture of claim 20 wherein the oily phase comprises silicone.

22. The mixture of claim 17 wherein the persulfate composition comprises, by weight of the total persulfate composition:
about 15–65% of one or more inorganic persulfates,
about 0.1–5% of one or more inorganic salts, and
about 5–60% of one or more particulate fillers.

23. The composition of claim 22 which is in the powdered form.

24. The composition of claim 22 which is in the cream or paste form.

25. The composition of claim 24 further comprising an oil which is a hydrophobic oil, a lipophilic ingredient or mixtures thereof.

26. The mixture of claim 17 wherein the bleach oil composition comprises, by weight of the total bleach oil composition:
about 1–75% water,
about 0.1–50% hydrophobic oil, and
about 0.1–50% of one or more alkalizing agents.

27. The composition of claim 26 wherein the hydrophobic oil is selected from the group consisting of coconut oil, mineral oil, isopropyl myristate, and mixtures thereof.

28. An emulsion hair bleach composition prepared by combining (i) an aqueous oxidizing agent composition, (ii) a persulfate composition containing at least one organic oil having a Hildebrand solubility parameter ranging from about 5 to 12 $(cal/cm^3)^{1/2}$, and (iii) a bleach oil composition in amounts sufficient to provide a mixture capable of lightening the hair in ten to thirty minutes.

29. A kit for use in bleaching hair comprising three separate components, wherein the first component is an aqueous oxidizing agent composition, the second component is a persulfate composition, and the third composition is a bleach oil composition wherein the persulfate composition contains at least one hydrophobic organic oil having a Hildebrand solubility parameter ranging from about 5 to 12 $(cal/cm^3)^{1/2}$; wherein when said three components are mixed they provide a mixture that lightens hair in ten to thirty minutes.

30. The kit of claim 1 wherein the aqueous oxidizing agent composition comprises about 20–80% by weight of the total mixture, the persulfate composition comprises about 5–40% by weight of the total mixture, and the bleach oil composition comprises about 10–30% by weight of the total mixture.

* * * * *